United States Patent
Tanaka et al.

(10) Patent No.: US 6,245,716 B1
(45) Date of Patent: Jun. 12, 2001

(54) BENZOYLPYRAZOLE COMPOUNDS AND HERBICIDE

(75) Inventors: Katsunori Tanaka; Hiroyuki Adachi, both of Odawara; Masami Koguchi, Higashiueno; Akihiro Takahashi, Minamiashigara, all of (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/673,776

(22) PCT Filed: Apr. 21, 1999

(86) PCT No.: PCT/JP99/02113

§ 371 Date: Oct. 18, 2000

§ 102(e) Date: Oct. 18, 2000

(87) PCT Pub. No.: WO99/54328

PCT Pub. Date: Oct. 28, 1999

(30) Foreign Application Priority Data

Apr. 22, 1998 (JP) .................................. 10-112358

(51) Int. Cl.$^7$ ........................ A61N 43/80; C07D 261/04
(52) U.S. Cl. ........................ 504/271; 548/240; 548/247
(58) Field of Search ................... 548/247, 240; 504/271

(56) References Cited

U.S. PATENT DOCUMENTS 4,931,565    6/1990   Baba et al. .
5,939,360    8/1999   Adachi et al. .
5,948,917    9/1999   Adachi et al. .

FOREIGN PATENT DOCUMENTS

| 03-044375B | 2/1991  | (JP) . |
| 97/41118   | 6/1997  | (WO) . |
| WO 97/41105 | 11/1997 | (WO) . |
| WO 97/41116 | 11/1997 | (WO) . |
| WO 97/41117 | 11/1997 | (WO) . |
| WO 97/46530 | 12/1997 | (WO) . |
| WO 98/31681 | 7/1998  | (WO) . |

*Primary Examiner*—Deborah C. Lambkin
*Assistant Examiner*—Andrea M D'Souza
(74) *Attorney, Agent, or Firm*—Louise A. Foutch; Dennis G. LaPointe; Mason & Assoc., P.A.

(57) ABSTRACT

Compounds represented by general formula (1) and a herbicide containing any of the compounds as the active ingredient, wherein $R^1$, $R^2$, and $R^3$ each independently represents halogeno, $C_{1-6}$ allyl, etc.; $R^4$ and $R^5$ each independently represents hydrogen, $C_{1-6}$ alkyl, etc.; and Het represents either an isoxazole group optionally substituted by $C_{1-4}$ alkyl or a derivative of the group.

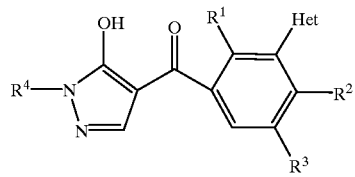

(1)

2 Claims, No Drawings

BENZOYLPYRAZOLE COMPOUNDS AND HERBICIDE

This application is a 371 of PCT/JP99/02113 Apr. 21, 1999.

FIELD OF INVENTION

The present invention is related to novel pyrazole compounds substituted with a specific benzoyl groups at the 4th position of the pyrazole ring and a herbicide.

BACKGROUND ART

For cultivation of agricultural and horticultural crops, many herbicides have been used for weed control, which requires enormous labors in the past. However, herbicides cause phytotoxicity to crops, residue in environment and spoil to the environment, and therefore, new herbicides capable of firmly controlling weeds with lower doses and using safely have been desired.

In WO96/26206, a herbicide represented by a general formula (A);

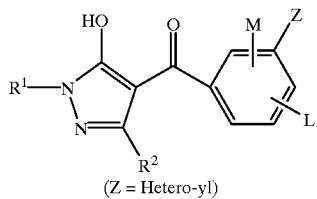

(A)

(Z = Hetero-yl)

wherein a benzoyl group is substituted at the 4$^{th}$ position of the pyrazole ring and a heterocyclic ring is substituted on the benzene ring, is disclosed.

Whereas, in WO97/46530, a herbicidal compound represented by a general formula (B) is disclosed.

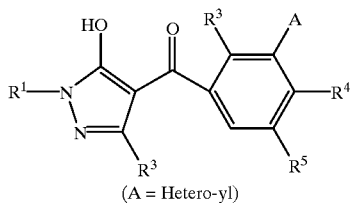

(B)

(A = Hetero-yl)

However, among such disclosed herbicidal compounds, only compounds of which heterocyclic ring represented by A is 1-methyl-1H-pyrazole-3-yl are disclosed with their physical data, and no biological activity data is described for those compounds.

Whereas, in WO97/41118, herbicidal compounds represented by a general formula (C) are disclosed.

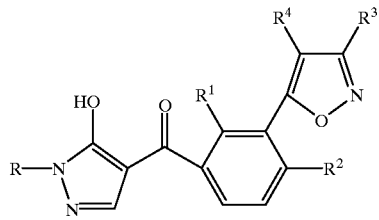

(C)

DISCLOSURE OF THE INVENTION

It is an object of the present invention to provide a herbicide, which can be synthesized advantageously in an industrial scale, giving firm herbicidal activity with lower doses, being used safely, having good selectivity in the activity for crops and weeds, and being composed of a novel pyrazole compound as the active ingredient.

The present invention is directed to a herbicide composed of a compound represented by a general formula (1);

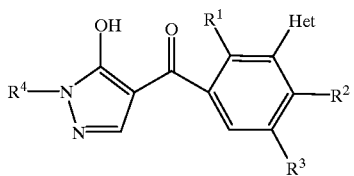

(1)

wherein $R^1$, $R^2$ and $R^3$ are each independently halogeno, $C_{1-6}$ alkyl, $C_{1-6}$ alkoxy, $C_{1-6}$ haloalkyl, $C_{1-6}$ haloalkoxy, $C_{1-6}$ alkylthio, $C_{1-6}$ alkylsulfinyl or $C_{1-6}$ alkylsulfonyl, $R^4$ and $R^5$ are each independently hydrogen, $C_{1-6}$ alkyl, $C_{1-6}$ alkenyl or $C_{1-6}$ alkynyl, Het is a substituent represented by the following formulas;

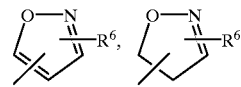

wherein $R^6$ represents hydrogen or $C_{1-4}$ alkyl, or the salt or 1 or more than 2 of the said compounds.

In the general formula (1) described above, Het represents isoxazole-3-yl, isoxazole-4-yl, isoxazole-5-yl, 4,5-dihydroisoxazole-3-yl, 4,5-dihydroisoxazole-4-yl, or 4,5-dihydroisoxazole-5-yl, all of which may be optionally-substituted.

For the example of Het, isoxazole-3-yl, isoxazole-4-yl, isoxazole-5-yl, 3-methylisoxazole-4-yl, 3-methylisoxazole-5-yl, 4-methylisoxazole-3-yl, 4-methylisoxazole-5-yl, 4,5-dihydroisoxazole-3-yl, 4,5-dihydroisoxazole-4-yl, 4,5-dihydroisoxazole-5-yl, 3-methyl-4,5-dihydroisoxazole-4-yl, 3-methyl-4,5-dihydroisoxazole-5-yl, 4-methyl-4,5-dihydroisoxazole-3-yl, 4-methyl-4,5-dihydroisoxazole-5-yl and the like can be preferably given.

In the general formula (1), $R^1$, $R^2$ and $R^3$ each independently represent halogeno, such as fluorine, chlorine, bromine and iodine, $C_{1-6}$ alkyl, such as methyl, ethyl, propyl, isopropyl, n-butyl, isobutyl, s-butyl and t-butyl, $C_{1-6}$ alkoxy, such as methoxy, ethoxy, propoxy, isopropoxy, butoxy and t-butoxy, $C_{1-6}$ haloalkyl, such as trifluoromethyl, trichloromethyl, fluoromethyl, chloromethyl, difluoromethyl, dichloromethyl, 2,2,2-trifluoroethyl and pentafluoroethyl, $C_{1-6}$ haloalkoxy, such as trifluoromethoxy, trichloromethoxy, difluoromethoxy and trifluoroethoxy, $C_{1-6}$ alkylthio, such as methylthio, ethylthio, propyltwio and isopropylthio, $C_{1-6}$ alkylsulfinyl, such as methylsulfinyl, ethylsulfinyl, propylsulfinyl and isopropylsulfinyl, and $C_{1-6}$ alkylsulfonyl, such as methylsulfonyl, ethylsulfonyl, propylsulfonyl and isopropylsulfonyl.

$R^4$ and $R^5$ each independently represent hydrogen, $C_{1-6}$ alkyl, such as methyl, ethyl, propyl, isopropyl, n-butyl, isobutyl, s-butyl and t-butyl, $C_{2-6}$ alkenyl, such as vinyl, 1-propenyl, allyl and 2-butenyl, and $C_{2-6}$ alkynyl, such as ethynyl, 1-propynyl and 2-propynyl.

$R^6$ represents $C_{1-4}$ alkyl, such as methyl, ethyl, propyl, isopropyl, n-butyl, isobutyl, s-butyl and t-butyl.

MODE FOR CARRYING OUT THE INVENTION

The compounds of the present invention are prepared according to a process shown in the following reaction diagram.

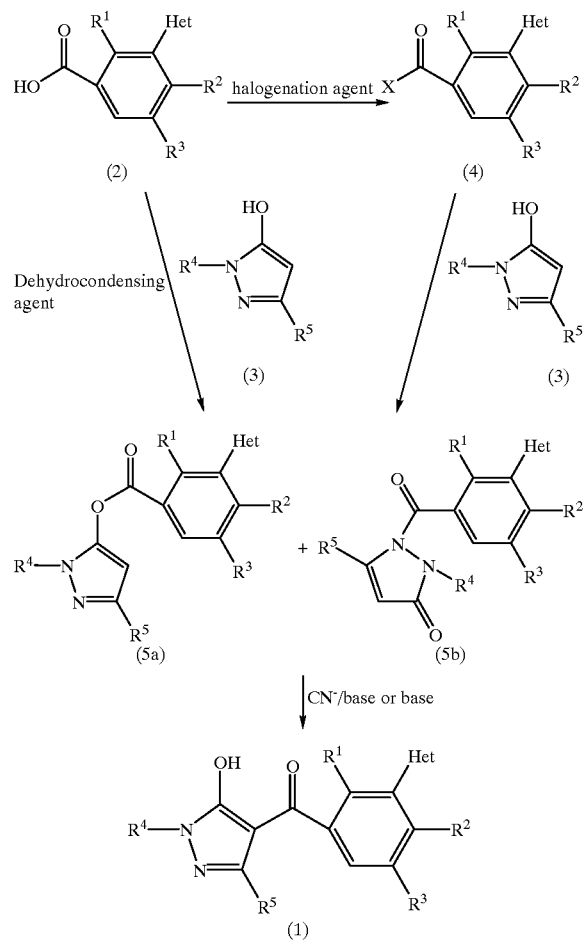

wherein $R^1$ through $R_5$ and Het are as defined above, and X represents a halogen atom.

In the process above, intermediates (5a) and (5b) are obtained by subjecting either a compound (2) or a compound (4) to a reaction with hydroxypyrazole (3), and then an objective compound (1) is obtained from the intermediates (5a) and (5b).

The compound (4) is prepared from the compound (2) according to generally-known synthetic chemical reaction using an inorganic halogenation agent, such as thionyl chloride and phosphorus pentachloride.

The intermediates (5a) and (5b) are obtainable by subjecting the compound (4) and the compound (3), each in an amount of 1 mole, or using either one in an excess amount, to a reaction in the presence of a base either in an amount of 1 mole or in an excess amount.

As the base used in the reaction, an alkali metal hydroxide, such as KOH and NaOH, an alkali metal carbonate, such as sodium carbonate and potassium carbonate, an alkaline earth metal hydroxide, such as calcium hydroxide and magnesium hydroxide, an alkaline earth metal carbonate such as calcium carbonate, a tertiary amine, such as triethyl amine and diisopropyl ethyl amine, an organic base such as pyridine, sodium phosphate and the like can be given.

As the solvent used in the reaction, water, dichloromethane, chloroform, toluene, ethyl acetate, N,N-dimethyl formamide (DMF), tetrahydrofuran (THF), dimethoxy ethane (DME), acetonitrile and the like can be used.

The mixture for the reaction is stirred until the completion of the reaction at a temperature of from 0° C. to the boiling point of the solvent used. Alternatively, the reaction can be performed in two solvents system by using a phase-transfer catalyst, such as quaternary ammonium salt.

Further, the compound (5a) and the compound (5b) are obtainable by subjecting the compounds (2) and (3) to a reaction in the presence of a dehydrating and condensing agent like dicyclohexylcarbodimide (DCC).

As examples for the solvent used in the reaction, dichloromethane, chloroform, toluene, ethyl acetate, DMF, THF, DME, acetonitrile, t-pentyl alcohol and the like can be given.

The mixture for the reaction is continuously stirred until the completion of the reaction at a temperature of from −10° C. to the boiling point of the solvent used and then processed according to common procedure.

The compound (5a) and the compound (5b) may be directly used as a mixture for the following rearrangement.

The rearrangement is carried out in the presence of a cyanide and a less reactive base. Namely, the compound (1) is obtainable by subjecting the compounds (5a) and (5b) each in an amount of 1 mole to a reaction with the base in an amount of from 1 to 4 moles, and preferably from 1 to 2 moles, and the cyanide in an amount of from 0.01 to 1.0 mole, and preferably from 0.05 to 0.2 mole.

As the base used in the reaction described above, alkali metal hydroxides, such as KOH and NaOH, alkali metal carbonates, such as sodium carbonate and potassium carbonate, alkaline earth metal hydroxides, such as calcium hydroxide and magnesium hydroxide, alkaline earth metal carbonate such as calcium carbonate, tertiary amines, such as triethyl amine and diisopropyl ethyl amine, organic bases such as pyridine, sodium phosphate and the like can be used.

As the cyanide used in the reaction described above, a polymer carrying any of potassium cyanide, sodium cyanide, acetone cyanohydrine, hydrogen cyanide and potassium cyanide and the like can be used. It is preferable to add a small amount of a phase-transfer catalyst, such as crown ether, into the reaction system as the phase-transfer catalyst can contribute to complete the reaction in a shorter time.

The solvent used in the reaction are dichloroethane, benzene, toluene, acetonitrile, chloroform, ethyl acetate, DMF, methyl isobutyl ketone, THF, DME and the like. The reaction may smoothly proceeds under a temperature lower than 80° C., and preferably at a temperature range of from an ambient temperature to 40° C.

Further, the rearrangement is also carried out in an inactive solvent in the presence of a base, such as potassium carbonate, sodium carbonate, triethyl amine and pyridine. The amount of the base to be used in the rearrangement is 0.5–2.0 moles based on the total amount of the compounds (5a) and (5b), and the solvent used in the reaction is any of THF, dioxane, t-pentyl alcohol, t-butyl alcohol, etc. The temperature applied for the reaction is in a range of from an ambient temperature to the boiling point of the solvent used.

Furthermore, the compound (1) is also obtainable from the compounds (3) and (2), without isolating the compound (5a) and the compound (5b), by using a base in combination with a dehydrating and condensing agent, such as DCC. The base used in this reaction are potassium carbonate, sodium carbonate, triethyl amine, pyridine or the like, and the amount of the base to be used in this reaction is 0.5–2.0 moles based on the amount of the compound (3). As the solvent used in this reaction, THF, dioxane, t-pentyl alcohol, t-butyl alcohol and the like can be used, and the temperature to be applied for this reaction is in a range of from an ambient temperature to the boiling point of the solvent used.

5-Hydroxypyrazoles represented by the general formula (3) can be prepared according to the following processes (a) and (b), which are described in JP Laid-open No. Sho 62-234069 and JP Laid-open No. Hei 3-44375, for examples.

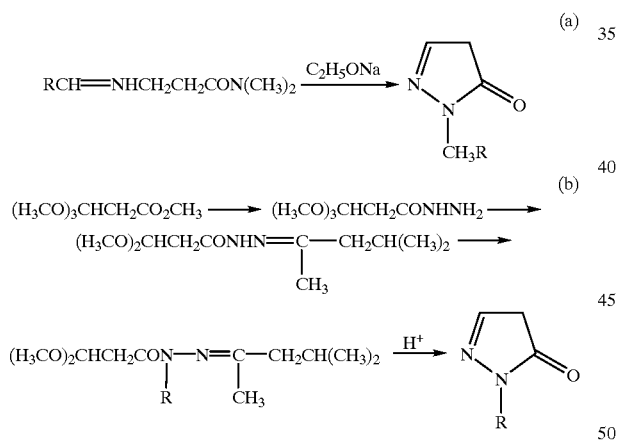

Among the compounds represented by the general formula (2), which are important intermediates for synthesizing the compounds according to the present invention, benzoic acids of which part represented by Het is 3-methylisoxazole-5-yl are obtainable according to the following process.

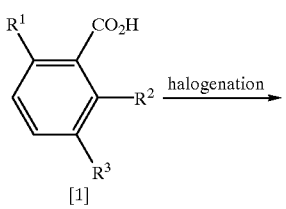

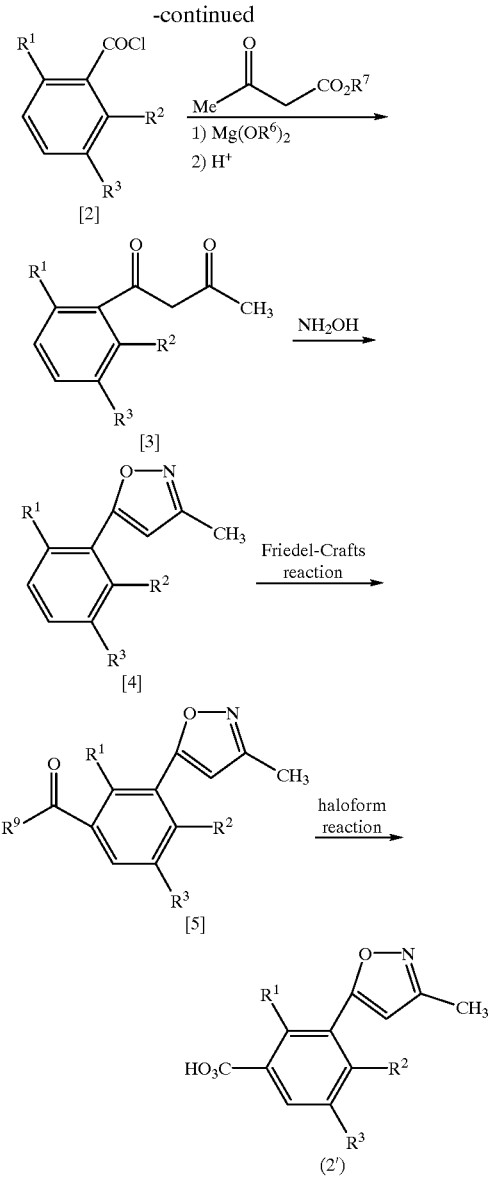

wherein $R^1$, $R^1$ and $R^3$ are as defined above, and $R^7$, $R^8$ and $R^9$ each independently represent a lower alkyl.

In the first step, the carboxylic acid form [1] is subjected to a reaction in an inactive solvent, such as hydrocarbons including benzene and toluene and halogenated hydrocarbons including methylene chloride and chloroform with a chlorinating agent, such as phosgene, thionyl chloride and oxalyl chloride, to prepare the carbonyl chloride [2].

Then, a magnesium salt, which is obtained by reacting acetoacetate ester with magnesium alcoholate, is subjected to a reaction with the carbonyl chloride [2] to hydrolyze and decarboxylate the ester, which leads to obtain the β-diketone form [3]. Further, the compound [4] can be obtained by reacting hydroxyl amine with the β-diketone form.

As the solvent used in the reaction described herein above, alcohols, such as methanol and ethanol, hydrocarbons, such as benzene and toluene, halogenated hydrocarbons, such as dichloromethane and chloroform, ethers, such as THF and dioxane, acetonitrile, DMF, pyridine, water, etc., and mixtures of 2 or more of these solvents can be used. The reaction is performed at a temperature ranging from 0° C. to the boiling point of the solvent used. In the reaction, an acid, such as sulfuric acid and p-toluenesulfonic acid, may be used as a catalyst.

Then, the compound [4] is acylated based on Frieder-Crafts reaction to obtain the compound [5], and the carboxylic acid form (2') is then prepared from the compound [5] based on haloform reaction.

Among the compounds represented by the general formula (2), which are the important intermediates for synthesizing the compounds according to the present invention, the benzoic acid form, of which part represented by Het is 4,5-dihydroisoxazole-3-yl, can be prepared according to the following process.

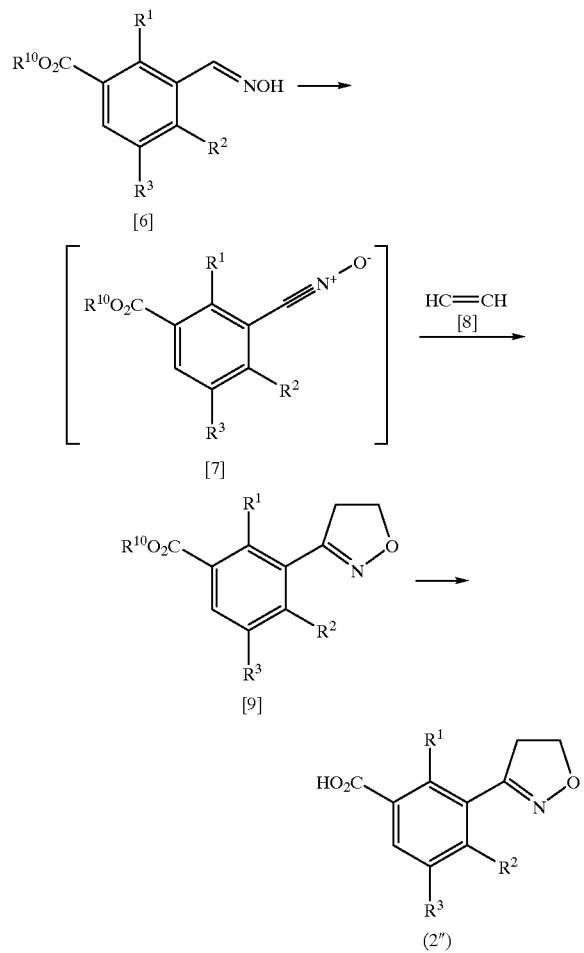

wherein $R^1$, $R^2$ and $R^3$ are as defined above, and $R^{10}$ represents lower alkyl.

The dihydroisoxazole form (2") is obtainable as follows. The aldoxime form [6] is reacted with a halogenating agent, such as chlorine, bromine, N-chlorosuccinimide (NCS) and N-bromosuccinimide (NBS) in a solvent selected from a group consisting of hydrocarbons including benzene and toluene, ethers including THF and dioxane, nitriles such as acetonitrile and DMF under a temperature of from −10 to 50° C. to obtain an intermediates. Then, the intermediate is reacted with an organic base such as triethyl amine or a carbonate base, such as sodium hydrogen carbonate and potassium carbonate, to obtain the nitrile oxide form [7]. Then, the nitrile oxide form [7] is reacted with ethylene [8] either under atmospheric pressure or under compressed pressure by using a compressing container like an autoclave at a temperature of from an ambient temperature to the boiling point of the solvent used to obtain the compound [9].

The compound [9] is then hydrolyzed according to a publicly-known process to obtain the dihydroisoxazole form (2"). Whereas, the nitrile oxide form [7] is also obtainable by subjecting the aldoxime form [6] to a reaction with a hypohalide such as sodium hypochloride.

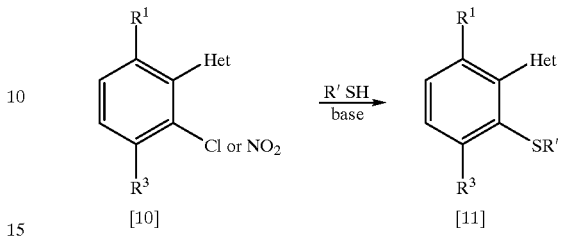

wherein $R^1$, $R^3$ and Het are as defined above, and R' represents $C_{1-6}$ alkyl.

Further, the benzoic acids, of which $R^2$ is alkylthio, are obtainable by reacting either Cl— or $NO_2$— form represented by the general formula [10] with an alkane thiol represented by a formula of R'SH in the presence of a base. In addition, upon requirement, the corresponding alkylsulfinyl and alkylsulfonyl forms are also obtainable by subjecting the benzoic acid to an oxidation reaction.

As examples for the base to be used for the reaction for obtaining the alkylthio form [11], alkali metal hydroxides, such as sodium hydroxide and potassium hydroxide, metal alkoxides, such as sodium methoxide and sodium ethoxide, carbonates, such as sodium carbonate and potassium carbonate, hydrides such as sodium hydride, and organic bases, such as triethyl amine, diisopropyl ethyl amine, 1,8-diazabicyclo[5,4,0]undece-7-ene (DBU) and pyridine, can be given. And, as examples for the solvent used in the said reaction, alcohols, such as methanol and ethanol, ethers, such as THF and DME, amides, such as DMF and dimethyl acetoamide, hydrocarbons, such as benzene, toluene and xylene, dimethyl sulfoxide, acetonitrile and the like can be given.

The following oxidation reaction is performed in an inactive solvent, such as water, an organic acid including acetic acid, or halogenated hydrocarbon, such as dichloromethane, chloroform and carbon tetrachloride, by using an oxidizing agent including peroxy acid, such as hydrogen peroxide, peracetic acid, perbenzoic acid and m-chloroperbenzoic acid, and hypochlorous acid, such as sodium hypochlorite and potassium hyprochlorite. This reaction proceeds smoothly under a temperature ranging from an ambient temperature to the boiling point of the solvent used.

Whereas, in case that the compound (1) contains a free hydroxy group therein, the salts, particularly the agriculturally and horticulturally acceptable salts, acylates, sulfonates, carbamates, ethers and thioethers of the compound (1) can be derived. As the preferable agriculturally and horticulturally acceptable salts, sodium salts, potassium salts, calcium salts and ammonium salts can be given as the examples.

As examples for the ammonium salt, a salt bonding to an ion represented by a formula of N+RaRbRcRd, wherein Ra, Rb, Rc and Rd are each independently hydrogen or $C_{1-10}$ alkyl substituted with hydroxy or the like, as the case may be, can be given. If any of Ra, Rb, Rc and Rd is a substituted alkyl, it is preferable that they contain 1–4 carbon atoms.

As example for the preferable acylate, ether and carbamate derivatives, the compound, of which OH part is converted to a group represented by any formula of —OCORe, —Orf and —OCONRgRh, wherein Re, Rf, Rg and Rh represent, for example, $C_{1-6}$ alkyl, allyl or phenyl those which are substituted as the case may be, can be given. These derivatives may be prepared according to a customarily-known process.

The compound (1) of the present invention may be obtained in forms of several types tautomers. And, all of those tautomers shall be included in the scope of the compounds according to the present invention.

tristyrylphenyl ether, sulfuric acid ester of alkylphenyl ether added with polyoxyethylene, alkyl benzene sulfonate, sulfuric acid ester of higher alcohol, alkyl sulfate, alkyl naphthalene sulfonate, polycarboxylate, lignin sulfonate, formaldehyde condensate of alkyl naphthalene sulfonate, co-polymer of isobutylene and maleic anhydride, etc. can be given.

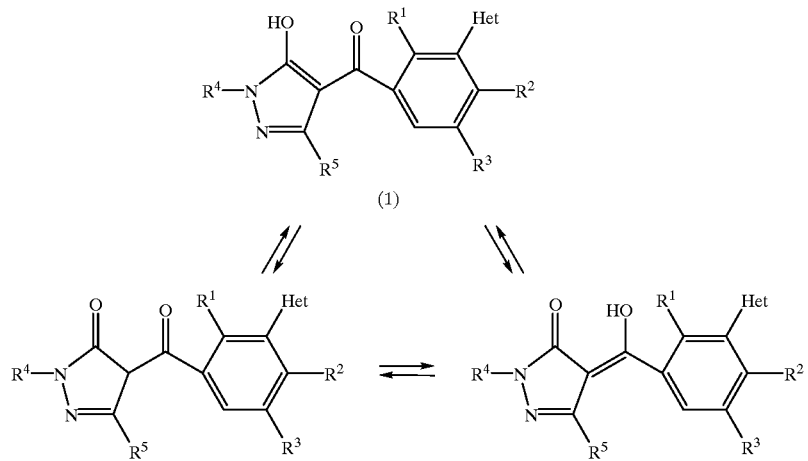

wherein $R^1$ through $R^5$ and Het are as defined above.

The compounds of the present invention and various intermediates for them are obtainable by subjecting the reacted products to ordinary post-reaction procedures after the specific reactions.

The structures of the compounds of the present invention and the intermediates described above are determined based on analysis by means of IR, NMR, MS, etc.

(Herbicide)

The herbicide according to the present invention contains one or more of the compounds of the present invention as the active ingredients. At practically applying the compound of the present invention, it may be directly applied in its purified form without adding any other ingredients, and it may be also applied in the form of general formulation for agricultural chemicals to be used as plant protection chemicals, such forms as wettable powder, granules, powder, emulsifiable concentrate, water soluble powder, suspension liquid and flowable concentrate. As additives and carriers, vegetative powder, such as soybean powder and wheat flour, mineral fine powder, such as diatomaceous earth, apatite, gypsum, talc, bentonite, pyrophyllite and clay, organic and inorganic compounds, such as sodium benzoate, urea and Glauber's salt, are usable for solid type formulations. For the liquid type formulations, petroleum fractions, such as kerosine, xylene and solvent naphtha, cyclohexane, cyclohexanone, DMF, DMSO, alcohol, acetone, trichloroethylene, methyl isobutyl ketone, mineral oil, vegetable oil, water and the like are used as a diluent. For the formulations described above, a surface active agent may be added into such formulations in order to secure providing uniform and stable preparations, if required. As example for the said surface active agent, though there is no limitation for the type, nonionic surface active agent, such as polyoxyethylene-added alkyl phenyl ether, polyoxyethylene-added alkyl ether, polyoxyethylene-added higher fatty acid ester, polyoxyethylene-added sorbitan higher fatty acid ester and polyoxyethylene-added The concentration of the active ingredient in the herbicide according to the present invention may be different upon the type of the formulations as described above, however, the concentration could be in a range of from 5 to 90% by weight, hereinafter "% by weight" is expressed by "%", and preferably from 10 to 85%, for the wettable powder, and it could be in a range of from 3 to 70%, and preferably from 5 to 60%, for the emulsifiable concentrate, and it could be in a range of from 0.01 to 50%, and preferably from 0.05 to 40%, for the granules.

The wettable powder and the emulsifiable concentrate obtained as described above are diluted with water to prepare into the suspension or the emulsion at a desired concentration and then applied either before or after germination of weeds, whereas, the granules are directly incorporated into the soil either before or after germination of weeds. For practical application of the herbicide according to the present invention, the appropriate amount of the active ingredients, which is at a rate of more than 0.1 g/ha, may be applied.

The herbicide according to the present invention is usable by mixing with known fungicides, insecticides, acaricides, herbicides, plant growth regulators and fertilizers. In particular, mixing with other herbicide allows to reduce the dose of the herbicide to use. In addition, such mixing may contribute not only for less labor requirement but also for giving higher herbicidal activity based on the synergistic effect given by the mixed herbicides. Further, combination with plurality of known herbicides is also practically useful.

As example for the suitable herbicides to be combined with the herbicide according to the present invention, anilide-type herbicides, such as diflufenican and propanil, chloroacetoanilide-type herbicides, such as alachlor and pretilachlor, aryloxyalkanic acid-type herbicides, such as 2,4-D and 2,4-DB, aryloxyphenoxyalkanic acid-type herbicides, such as diclofop-methyl and fenoxaprop-ethyl, arylcarboxylic acid-type herbicides, such as dicamba and pyrithiobac, imidazolynon-type herbicides, such as imazaquin and imazethapyr, urea-type herbicides, such as diuron and isoproturon, carbamate-type herbicides, such as chlorprophame and phenmedipham, thiocarbamate-type herbicides, such as thiobencarb and EPTC, dinitroaniline-type herbicides, such as trifluralin and pendimethaline, diphenyl ether-type herbicides, such as acilfluorfen and fomesafen, sulfonylurea-type herbicides, such as bensulfuron-methyl and nicosulfuron, triazinone-type herbicides, such as metribuzin and metamitron, triazine-type herbicides, such as atrazine and cyanazine, triazopirimidine-type herbicides, such as flumetsulam, nitrile-type herbicides, such as bromoxynil and dichlobenil, phosphoric acid-type herbicides, such as glyphosate and glufosinate, quaternary ammonium salt-type herbicides, such as paraquat and difenzoquat, cyclic amide-type herbicides, such as flumiclorac-pentyl and fluthiaset-methyl, isoxaben, ethofumesate, oxadiazon, quinclorac, clomazone, sulcotrione, simetryn, dithiopyr, pyrazolate, pyridate, flupoxam, bentazon, benfuresate, and cyclohexandione-type herbicides, such as sethoxydim and tralkoxydim, can be given. Also, it is useful to add vegetative oil and oil concentrate to combinations with any of these herbicides.

BEST MODE FOR CARRYING OUT THE INVENTION

Now, the present invention is further described in detail with referring the Examples and Reference Examples described below.

EXAMPLE 1

Preparation of 4-[2,5-dimethyl-3-(3-methylisoxazole-5-yl)-4-methanesulfonyl] benzoyl-1-methyl-5-hydroxypyrazole (Compound No. 11)

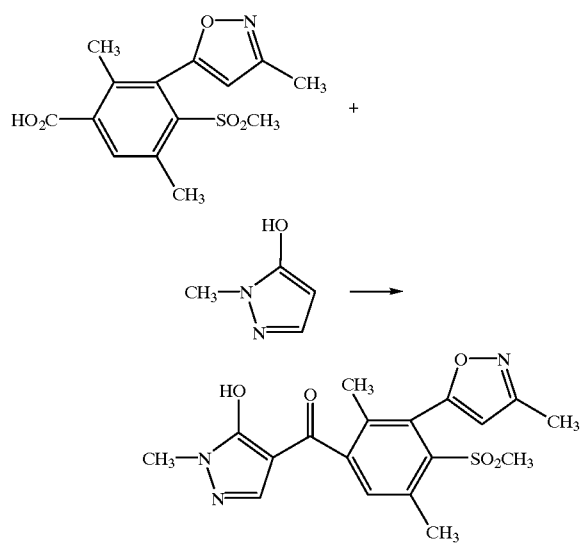

2,5-Dimethyl-3-(3-methylisoxazole-5-yl)-4-methanesulfonylbenzoic acid in an amount of 0.50 g (1.6 mmol) was dissolved in 10 ml benzene, and the resulting solution was then added with thionyl chloride in an amount of 0.29 g (2.4 mmol) and two drops of pyridine and was stirred for 2 hours under heating and reflux. After distillating out the solvent in the solution under reduced pressure, the residue was dissolved in 3 ml chloroform and the resulting solution was added dropwise into a mixture of 1-methyl-5-hydroxypyrazole hydrochloride in an amount of 0.26 g (1.9 mmol), 5ml chloroform and triethyl amine in an amount of 0.38 g (3.8 mmol) while cooling with ice. After stirring the mixture for 30 minutes at an ambient temperature, the mixture was further added with acetone cyanohydrine in an amount of 0.05 g (0.6 mmol) and triethyl amine in an amount of 0.33 g (3.3 mmol) and was further stirred overnight at an ambient temperature. The reacted solution was then washed with 1N-hydrochloric acid and then with saturated brine, then dried with anhydrous magnesium sulfate, and consequently, the solvent therein was distillated out. The crystals remained was washed with methanol to obtain the objective compound in an amount of 0.38 g in crystalline form. Mp. 208–213° C.

EXAMPLE 2

Preparation of 4-[4,5-Dichloro-2-methyl-3-(3-methylisoxazole-5-yl) benzoyl-1-methyl- 5-hydroxypyrazole (Compound No. 9)

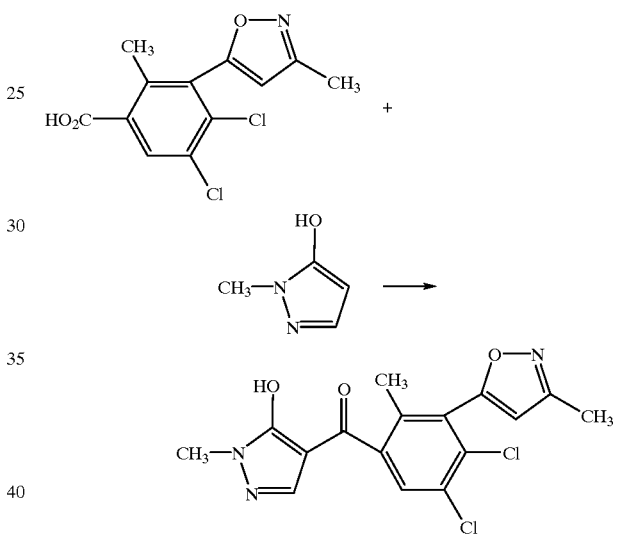

4,5-Dichloro-2-methyl-3-(3-methylisoxazole-5-yl) benzoic acid in an amount of 0.35 g (1.2 mmol) was dissolved in 10 ml benzene, and the resulting solution was then added with thionyl chloride in an amount of 0.18 g (1.5 mmol) and one drop of pyridine and was stirred for 2 hours under heating and reflux. After distillating out the solvent from the reacted mixture under reduced pressure, the residue was dissolved in 3 ml chloroform and the resulting solution was added dropwise into a mixture of 1-methyl-5-hydroxypyrazole hydrochloride in an amount of 0. 19 g (1.4 mmol), 4 ml chloroform and triethyl amine in an amount of 0.26 g (2.6 mmol) while cooling with ice. After stirring the mixture for 30 minutes at an ambient temperature, the mixture was further added with acetone cyanohydrine in an amount of 0.03 g (0.4 mmol) and triethyl amine in an amount of 0.23 g (2.3 mmol) and was further stirred overnight at an ambient temperature. The reacted solution was washed with 1N-hydrochloric acid and then with saturated brine, then dried with anhydrous magnesium sulfate, and the solvent therein was distillated out. The obtained crystals were washed with methanol to obtain the objective compound in an amount of 0.33 g in crystalline form. Mp. 171–173° C.

REFERENCE EXAMPLE 1

Preparation of 2,5-Dimethyl-3-(3-methylisoxazole-5-yl)-4-methanesulfonylbenzoic acid

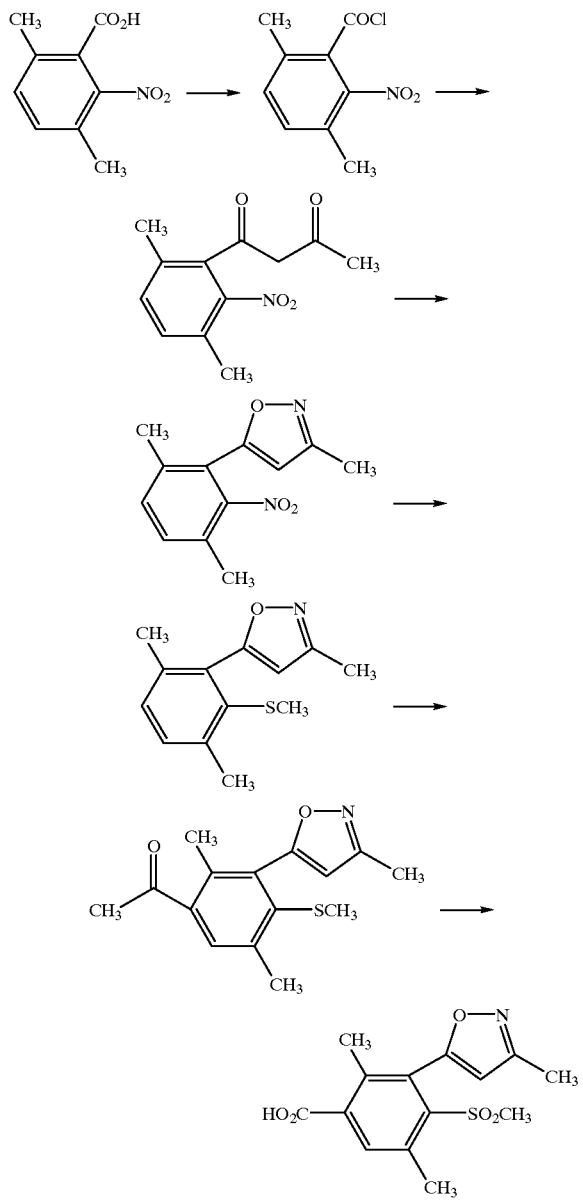

3,6-Dimethyl-2-nitrobenzoic acid in an amount of 9.6 g (51 mmol) was dissolved in 100 ml benzene and then followed by an addition of thionyl chloride in an amount of 8.8 g (74 mmol) and pyridine in an amount of 0.1 lg. The mixture was then heated for 2 hours under reflux, and the solvent therein was distillated out under reduced pressure to obtain 3,6-dimethyl-2-nitrobenzoyl chloride in an amount of 10.3 g.

Then, acetoacetate t-butyl ester in an amount of 8.9 g (56 mmol) was added into 80 ml toluene solution containing magnesium ethylate in an amount of 6.4 g (56 mmol) and the resulting mixture was stirred for 2 hours at 80° C., cooled down to an ambient temperature and added dropwise with 15 ml toluene solution of 3,6-dimethyl-2-nitrobenzoyl chloride in an amount of 10.3 g. The obtained mixture was stirred for 2 hours under heating and reflux, added with 10% sulfuric acid and extracted with ethyl acetate. The resulting organic solvent layer was washed with water and dried with anhydrous magnesium sulfate, and the solvent therein was distillated out under reduced pressure. The residue obtained was dissolved in 100 ml benzene and added with p-toluene sulfonic acid in an amount of 4.9 g (26 mmol), and the mixture was stirred for 2 hours under heating and reflux. Then, the reacted solution was washed with water and dried with anhydrous magnesium sulfate, and the solvent in the reacted solution was distillated out under reduced pressure. The residue obtained was purified by means of silica gei column chromatography to obtain 3,6-dimethyl-2-nitrobenzoylacetone in an amount of 3.9 g.

3,6-Dimethyl-2-nitrobenzoylacetone in an amount of 3.9 g (17 mmol) was dissolved in 50 ml ethanol and was then added with hydroxylamine hydrochloride in an amount of 1.8 g (26 mmol), and the obtained mixture was heated and subjected to reflux for 2 hours. The reacted solution was added with water and extracted with ethyl acetate, and the resulting organic solvent layer was dried with anhydrous magnesium sulfate, and the solvent in the solution was distillated out under reduced pressure, thereby obtaining 3,6-dimethyl-2-(3-methylisoxazole-5-yl)nitrobenzene in an amount of 3.3 g. Then, potassium t-butoxide in an amount of 4.8 g (43 mmol) was dissolved in 15 ml DMF, and methane thiol in an amount of 3.4 g (71 mmol) was then insufflated into the solution with ice-cooling. The solution was then added dropwise with 3 ml DMF solution of 3,6-dimethyl-2-(3-methylisoxazole-5-yl)nitrobenzene in an amount of 3.3 g (14 mmol). After stirring the solution for one hour at 40° C., the solution was poured into ice water and then extracted with dichloromethane. The resulting organic solvent layer was washed with saturated brine and dried with anhydrous magnesium sulfate, and the solvent therein was distillated out under reduced pressure, thereby obtaining 3,6-dimethyl-2-(3-methylisoxazole-5-yl)methylthiobenzene in an amount of 2.7 g.

3,6-Dimethyl-2-(3-methylisoxazole-5-yl) methylthiobenzene in an amount of 2.7 g (12 mmol) was dissolved in 5 ml dichloromethane, and the resulting solution was then added with acetyl chloride in an amount of 2.7 g (34 mmol). The mixture was then added dropwise into 25 ml dichloromethane suspension of aluminium chloride in an amount of 4.6 g (34 mmol) under cooling with ice, and the resulting mixture was stirred overnight at the ambient temperature. The reacted mixture was poured into ice water and subjected to an extraction with dichloromethane, and the resulting organic solvent layer was washed with water, dehydrated with anhydrous magnesium sulfate, and the solvent in the organic solvent layer was distillated out under reduced pressure, thereby obtaining 2,5-dimethyl-4-methylthio-3-(3-methylisoxazole-5-yl)acetophenone in an amount of 2.9 g.

2,5-Dimethyl-4-methylthio-3-(3-methylisoxazole-5-yl) acetophenone in an amount of 2.9 g (10 mmol) was dissolved in 25 ml dioxane. The resulting solution was then added dropwise with 10% sodium hypochlorite in an amount of 43 g (57 mmol) and was stirred for 3 hours at 80° C. After the completion of the reaction, the reacted solution was washed with chloroform and added with hydrochloric acid, and the crystals precipitated were filtrated and washed with water to obtain the objective compound, 2,5-dimethyl-3-(3-methylisoxazole-5-yl)-4-methanesulfonylbenzoic acid in an amount of 2.3 g.

1H-NMR(CDCl3, δ ppm): 2.34(3H, s), 2.44(3H, s), 2.81 (3H, s), 3.08(3H, s), 6.28(1H, s), 8.02(1H, s)

The representative examples for the compounds according to the present invention including the compounds specified in the Examples described above are presented in Table 1. In the column for Het in the table, the following markings are given for each group for abbreviation.

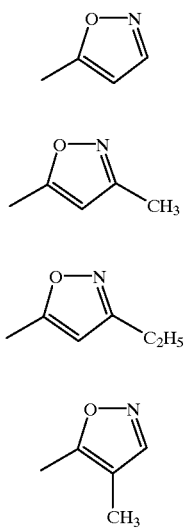

H-1

H-2

H-3

H-4

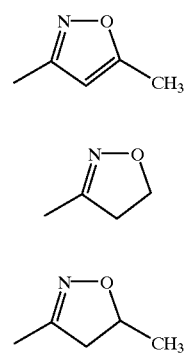

H-5

H-6

H-7

H-8

TABLE 1

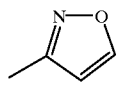

| Compound No. | R¹ | R² | R³ | R⁴ | R⁵ | Het | Physical value [ ] m.p. |
|---|---|---|---|---|---|---|---|
| 1 | $CH_3$ | Cl | Cl | $CH_3$ | H | H-1 | |
| 2 | $CH_3$ | $SO_2CH_3$ | Cl | $CH_3$ | H | H-1 | |
| 3 | $CH_3$ | $SO_2CH_3$ | $CH_3$ | $CH_3$ | H | H-1 | |
| 4 | $CH_3$ | $SO_2CH_3$ | $CH_3$ | $C_2H_5$ | H | H-1 | |
| 5 | Cl | Cl | $CH_3$ | $CH_3$ | H | H-1 | |
| 6 | Cl | $SO_2CH_3$ | $CH_3$ | $CH_3$ | H | H-1 | |
| 7 | $CH_3$ | $SO_2CH_3$ | $CH_3$ | $CH_3$ | $CH_3$ | H-1 | |
| 8 | $CH_3$ | $SO_2CH_3$ | $C_2H_5$ | $CH_3$ | H | H-1 | |
| 9 | $CH_3$ | Cl | Cl | $CH_3$ | H | H-2 | [171–173] |
| 10 | $CH_3$ | $SO_2CH_3$ | Cl | $CH_3$ | H | H-2 | [192–196] |
| 11 | $CH_3$ | $SO_2CH_3$ | $CH_3$ | $CH_3$ | H | H-2 | [208–213] |
| 12 | $CH_3$ | $SO_2CH_3$ | $CH_3$ | $C_2H_5$ | H | H-2 | [175–179] |
| 13 | Cl | Cl | $CH_3$ | $CH_3$ | H | H-2 | |
| 14 | Cl | $SO_2CH_3$ | $CH_3$ | $CH_3$ | H | H-2 | |
| 15 | $CH_3$ | $SO_2CH_3$ | $CH_3$ | $CH_3$ | $CH_3$ | H-2 | |
| 16 | $CH_3$ | $SO_2CH_3$ | $C_2H_5$ | $CH_3$ | H | H-2 | |
| 17 | $CH_3$ | Cl | Cl | $CH_3$ | H | H-3 | |
| 18 | $CH_3$ | $SO_2CH_3$ | Cl | $CH_3$ | H | H-3 | |
| 19 | $CH_3$ | $SO_2CH_3$ | $CH_3$ | $CH_3$ | H | H-3 | |
| 20 | $CH_3$ | $SO_2CH_3$ | $CH_3$ | $C_2H_5$ | H | H-3 | |
| 21 | Cl | Cl | $CH_3$ | $CH_3$ | H | H-3 | |
| 22 | Cl | $SO_2CH_3$ | $CH_3$ | $CH_3$ | H | H-3 | |
| 23 | $CH_3$ | $SO_2CH_3$ | $CH_3$ | $CH_3$ | $CH_3$ | H-3 | |
| 24 | $CH_3$ | $SO_2CH_3$ | $C_2H_5$ | $CH_3$ | H | H-3 | |
| 25 | $CH_3$ | Cl | Cl | $CH_3$ | H | H-4 | |
| 26 | $CH_3$ | $SO_2CH_3$ | Cl | $CH_3$ | H | H-4 | |
| 27 | $CH_3$ | $SO_2CH_3$ | $CH_3$ | $CH_3$ | H | H-4 | |
| 28 | $CH_3$ | $SO_2CH_3$ | $C_2H_5$ | $CH_3$ | H | H-4 | |
| 29 | Cl | Cl | $CH_3$ | $CH_3$ | H | H-4 | |

TABLE 1-continued

| Compound No. | R¹ | R² | R³ | R⁴ | R⁵ | Het | Physical value [ ] m.p. |
|---|---|---|---|---|---|---|---|
| 30 | Cl | SO$_2$CH$_3$ | CH$_3$ | CH$_3$ | H | H-4 | |
| 31 | CH$_3$ | SO$_2$CH$_3$ | CH$_3$ | CH$_3$ | CH$_3$ | H-4 | |
| 32 | CH$_3$ | SO$_2$CH$_3$ | C$_2$H$_5$ | CH$_3$ | H | H-4 | |
| 33 | CH$_3$ | Cl | Cl | CH$_3$ | H | H-5 | |
| 34 | CH$_3$ | SO$_2$CH$_3$ | Cl | CH$_3$ | H | H-5 | |
| 35 | CH$_3$ | SO$_2$CH$_3$ | CH$_3$ | CH$_3$ | H | H-5 | |
| 36 | CH$_3$ | SO$_2$CH$_3$ | CH$_3$ | C$_2$H$_5$ | H | H-5 | |
| 37 | Cl | Cl | CH$_3$ | CH$_3$ | H | H-5 | |
| 38 | Cl | SO$_2$CH$_3$ | CH$_3$ | CH$_3$ | H | H-5 | |
| 39 | CH$_3$ | SO$_2$CH$_3$ | CH$_3$ | CH$_3$ | CH$_3$ | H-5 | |
| 40 | CH$_3$ | SO$_2$CH$_3$ | C$_2$H$_5$ | CH$_3$ | H | H-5 | |
| 41 | CH$_3$ | Cl | Cl | CH$_3$ | H | H-6 | |
| 42 | CH$_3$ | SO$_2$CH$_3$ | Cl | CH$_3$ | H | H-6 | |
| 43 | CH$_3$ | SO$_2$CH$_3$ | CH$_3$ | CH$_3$ | H | H-6 | |
| 44 | CH$_3$ | SO$_2$CH$_3$ | CH$_3$ | C$_2$H$_5$ | H | H-6 | |
| 45 | Cl | Cl | CH$_3$ | CH$_3$ | H | H-6 | |
| 46 | Cl | SO$_2$CH$_3$ | CH$_3$ | CH$_3$ | H | H-6 | |
| 47 | CH$_3$ | SO$_2$CH$_3$ | CH$_3$ | CH$_3$ | CH$_3$ | H-6 | |
| 48 | CH$_3$ | SO$_2$CH$_3$ | C$_2$H$_5$ | CH$_3$ | H | H-6 | |
| 49 | CH$_3$ | Cl | Cl | CH$_3$ | H | H-7 | |
| 50 | CH$_3$ | SO$_2$CH$_3$ | Cl | CH$_3$ | H | H-7 | |
| 51 | CH$_3$ | SO$_2$CH$_3$ | CH$_3$ | CH$_3$ | H | H-7 | |
| 52 | CH$_3$ | SO$_2$CH$_3$ | CH$_3$ | C$_2$H$_5$ | H | H-7 | |
| 53 | Cl | Cl | CH$_3$ | CH$_3$ | H | H-7 | |
| 54 | Cl | SO$_2$CH$_3$ | CH$_3$ | CH$_3$ | H | H-7 | |
| 55 | CH$_3$ | SO$_2$CH$_3$ | CH$_3$ | CH$_3$ | CH$_3$ | H-7 | |
| 56 | CH$_3$ | SO$_2$CH$_3$ | C$_2$H$_5$ | CH$_3$ | H | H-7 | |
| 57 | CH$_3$ | Cl | Cl | CH$_3$ | H | H-8 | |
| 58 | CH$_3$ | SO$_2$CH$_3$ | Cl | CH$_3$ | H | H-8 | |
| 59 | CH$_3$ | SO$_2$CH$_3$ | CH$_3$ | CH$_3$ | H | H-8 | |
| 60 | CH$_3$ | SO$_2$CH$_3$ | CH$_3$ | C$_2$H$_5$ | H | H-8 | |
| 61 | Cl | Cl | CH$_3$ | CH$_3$ | H | H-8 | |
| 62 | Cl | SO$_2$CH$_3$ | CH$_3$ | CH$_3$ | H | H-8 | |
| 63 | CH$_3$ | SO$_2$CH$_3$ | CH$_3$ | CH$_3$ | CH$_3$ | H-8 | |
| 64 | CH$_3$ | SO$_2$CH$_3$ | C$_2$H$_5$ | CH$_3$ | H | H-8 | |
| 65 | Cl | SCH$_3$ | CH$_3$ | CH$_3$ | H | H-1 | |
| 66 | Cl | SCH$_3$ | CH$_3$ | CH$_3$ | H | H-1 | |
| 67 | Cl | SCH$_3$ | CH$_3$ | CH$_3$ | H | H-2 | |
| 68 | Cl | SCH$_3$ | CH$_3$ | CH$_3$ | H | H-2 | |
| 69 | Cl | SOCH$_3$ | CH$_3$ | CH$_3$ | H | H-1 | |
| 70 | Cl | SOCH$_3$ | CH$_3$ | CH$_3$ | H | H-1 | |
| 71 | Cl | SOCH$_3$ | CH$_3$ | CH$_3$ | H | H-2 | |
| 72 | Cl | SOCH$_3$ | CH$_3$ | CH$_3$ | H | H-2 | |
| 73 | F | SO$_2$CH$_3$ | CH$_3$ | CH$_3$ | H | H-1 | |
| 74 | F | SO$_2$CH$_3$ | CH$_3$ | CH$_3$ | H | H-1 | |
| 75 | F | SO$_2$CH$_3$ | CH$_3$ | CH$_3$ | H | H-2 | |
| 76 | F | SO$_2$CH$_3$ | CH$_3$ | CH$_3$ | H | H-2 | |
| 77 | OCH$_3$ | SO$_2$CH$_3$ | CH$_3$ | CH$_3$ | H | H-1 | |
| 78 | OCH$_3$ | SO$_2$CH$_3$ | CH$_3$ | CH$_3$ | H | H-1 | |
| 79 | OCH$_3$ | SO$_2$CH$_3$ | C$_2$H$_5$ | CH$_3$ | H | H-2 | |
| 80 | OCH$_3$ | SO$_2$CH$_3$ | C$_2$H$_5$ | CH$_3$ | H | H-2 | |
| 81 | CF$_3$ | SO$_2$CH$_3$ | CH$_3$ | CH$_3$ | CH$_3$ | H-1 | |
| 82 | CF$_3$ | SO$_2$CH$_3$ | C$_2$H$_5$ | CH$_3$ | H | H-1 | |
| 83 | CF$_3$ | SO$_2$CH$_3$ | CH$_3$ | CH$_3$ | CH$_3$ | H-2 | |
| 84 | CF$_3$ | SO$_2$CH$_3$ | C$_2$H$_5$ | CH$_3$ | H | H-2 | |
| 85 | OCF$_3$ | SO$_2$CH$_3$ | CH$_3$ | CH$_3$ | CH$_3$ | H-1 | |
| 86 | OCF$_3$ | SO$_2$CH$_3$ | C$_2$H$_5$ | CH$_3$ | H | H-1 | |
| 87 | OCF$_3$ | SO$_2$CH$_3$ | CH$_3$ | CH$_3$ | CH$_3$ | H-2 | |
| 88 | OCF$_3$ | SO$_2$CH$_3$ | C$_2$H$_5$ | CH$_3$ | H | H-2 | |
| 89 | Cl | SO$_2$C$_2$H$_5$ | CH$_3$ | CH$_3$ | CH$_3$ | H-1 | |
| 90 | Cl | SO$_2$C$_2$H$_5$ | C$_2$H$_5$ | CH$_3$ | H | H-1 | |
| 91 | Cl | SO$_2$C$_2$H$_5$ | CH$_3$ | CH$_3$ | CH$_3$ | H-2 | |
| 92 | Cl | SO$_2$C$_2$H$_5$ | C$_2$H$_5$ | CH$_3$ | H | H-2 | |
| 93 | Cl | SO$_2$Pr | CH$_3$ | CH$_3$ | CH$_3$ | H-1 | |
| 94 | Cl | SO$_2$Pr | C$_2$H$_5$ | CH$_3$ | H | H-1 | |
| 95 | Cl | SO$_2$iPr | CH$_3$ | CH$_3$ | CH$_3$ | H-2 | |

TABLE 1-continued

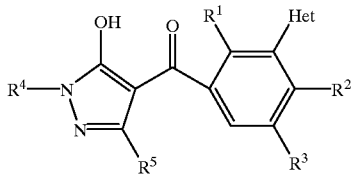

| Compound No. | R¹ | R² | R³ | R⁴ | R⁵ | Het | Physical value [ ] m.p. |
|---|---|---|---|---|---|---|---|
| 96 | Cl | SO₂tBu | C₂H₅ | CH₃ | H | H-2 | |
| 97 | Cl | SO₂nBu | C₂H₅ | CH₃ | H | H-2 | |
| 98 | Cl | OCH₃ | CH₃ | CH₃ | H | H-1 | |
| 99 | Cl | OCH₃ | C₂H₅ | CH₃ | H | H-1 | |
| 100 | Cl | OC₂H₅ | CH₃ | CH₃ | H | H-2 | |
| 101 | Cl | OC₂H₅ | C₂H₅ | CH₃ | H | H-2 | |
| 101 | Cl | OC₂H₅ | C₂H₅ | CH₃ | H | H-2 | |
| 102 | Cl | CH₂CH=CH | CH₃ | CH₃ | H | H-1 | |
| 103 | Cl | CH₂CH=CH | C₂H₅ | CH₃ | H | H-1 | |
| 104 | Cl | CH₂CH=CH | CH₃ | CH₃ | H | H-2 | |
| 105 | Cl | CH₂CH=CH | C₂H₅ | CH₃ | H | H-2 | |
| 106 | Cl | C≡CH | CH₃ | CH₃ | CH₃ | H-1 | |
| 107 | Cl | C≡CH | C₂H₅ | CH₃ | H | H-1 | |
| 108 | Cl | C≡CH | CH₃ | CH₃ | CH₃ | H-2 | |
| 109 | Cl | C≡CH | C₂H₅ | CH₃ | H | H-2 | |
| 110 | Cl | SO₂CH₃ | CF₃ | CH₃ | CH₃ | H-1 | |
| 111 | Cl | SO₂CH₃ | CF₃ | CH₃ | H | H-1 | |
| 112 | Cl | SO₂CH₃ | CF₃ | CH₃ | CH₃ | H-2 | |
| 113 | Cl | SO₂CH₃ | CF₃ | CH₃ | H | H-2 | |
| 114 | Cl | SO₂CH₃ | OCH₃ | CH₃ | CH₃ | H-1 | |
| 115 | Cl | SO₂CH₃ | OCH₃ | CH₃ | H | H-1 | |
| 116 | Cl | SO₂CH₃ | OCH₃ | CH₃ | H | H-2 | |
| 117 | Cl | SO₂CH₃ | OCH₃ | CH₃ | H | H-2 | |
| 118 | Cl | SO₂CH₃ | C₃H₇ | CH₃ | H | H-2 | |
| 119 | Cl | SO₂CH₃ | SCH₃ | CH₃ | H | H-1 | |
| 120 | Cl | SO₂CH₃ | SOCH₃ | CH₃ | H | H-2 | |
| 121 | Cl | SO₂CH₃ | SO₂CH₃ | CH₃ | H | H-2 | |
| 122 | Cl | SO₂CH₃ | Br | CH₃ | H | H-2 | |

(Herbicide)

Now, examples for the formulations for the herbicide according to the present invention is described below, however, the compound as the active ingredients, the type of the additives and the additional rate should not be limited to the ones described in the following examples, and those conditions can be modified over the wide range. The part indicated in the formulation examples represents part by weight.

[0094]

Example 3: Wettable Powder

| | |
|---|---|
| Compound of Invention | 20 parts |
| White Carbon | 20 parts |
| Diatomaceous Earth | 52 parts |
| Sodium Alkylsulfate | 8 parts |

All materials described above are mixed and pulverized into fine powder to obtain wettable powder formulation containing the active ingredient at a rate of 20%.

[0095]

Example 4: Emulsifiable Concentrate

| | |
|---|---|
| Compound of Invention | 20 parts |
| Xylene | 55 parts |
| N,N-dimethylformamide | 15 parts |
| Polyoxyethylenephenyl ether | 10 parts |

All materials described above are mixed and prepared into solution to obtain emulsifiable concentrate formulation containing the active ingredient at a rate of 20%.

[0096]

Example 5: Granules

| | |
|---|---|
| Compound of Invention | 5 parts |
| Talc | 40 parts |
| Clay | 38 parts |
| Bentonite | 10 parts |
| Sodium Alkylsulfate | 7 parts |

All materials described above are mixed, pulverized into fine particles, and granulated into granules having a diameter ranging from 0.5 to 1.0 mm to obtain granule formulation containing the active ingredient at a rate of 5%.

Industrial Use of the Invention

The compounds of the present invention show to have high herbicidal activity in both application methods of soil application and foliar application against various types of weeds in field crops, such as Xanthium strumarium, giant foxtail, velvet leaf, and Amaranthus blitum.

In the compounds of the present invention, the compounds, which can selectively control weeds grown in crop fields, such as maize, cereals including wheat and barley, soybean and cotton, are also included.

Further, in the compounds of the present invention, the compounds, which have plant growth regulating activity like growth retardant activity to useful plants, such as agricultural crops, ornamental plants and fruit trees, are also included.

Further, in the compounds of the present invention, the compounds, which have excellent selective herbicidal activity against weeds in paddy rice fields, such as cockspur grass, Cyperus difformis, water plantain, and Scirpus juncoides.

In addition, the compounds of the present invention can be also applied for weed control in orchards, lawns, side land of railways, clear spaces, etc.

In the compounds of the present invention, the compounds, which have plant growth regulating activity, fungicidal activity, and insecticidal and acaricidal activities, are also included.

Now, test examples for showing the herbicidal activity of the herbicide according to the present invention are described in the following.

Assessment of the herbicidal effect in the following test examples are performed based on the criterion described below and the effect was represented by index for weeds killed.

| Criterion for Assessment: | |
|---|---|
| % Weeds Killed | Index for Weeds Killed |
| 0% | 0 |
| 20–29% | 2 |
| 40–49% | 4 |
| 60–69% | 6 |
| 80–89% | 8 |
| 100% | 10 |

The index numbers, 1, 3, 5, 7 and 9 represent the intermediate effect between 0–2, 2–4, 4–6 and 8–10, respectively.

% Weeds Killed=(Fresh Weed Weight Overground in Untreated Plot−Fresh Weeds Weight Overground in Treated Plot)÷Fresh Weed Weight Overground in Untreated Plot)×100

As the compounds for the comparison, the compounds represented by the following chemical structures are provided.

A: Compound described in WO97/46530 gazette

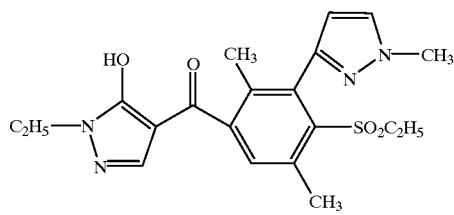

B: Compound described in WO97/41118 gazette

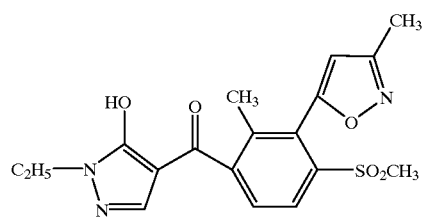

Test Example 1: Foliar Application in Upland Crop

A pot having the opening area of 200 $cm^2$ was filled with soil, and each seeds of plants including velvet leaf, Amaranthus blitum, Xanthium strumarium, giant foxtail, maize and wheat are planted onto the surface of the soil. The seeds were then covered with slight amount of soil and were placed in a greenhouse to grow. When each of the plants has grown to a height of from 5 to 25 cm, water dilution of the emulsifiable concentrate specified in the Example 4 and prepared at a desired dose of the active ingredients was sprayed onto the foliar parts of the plants by using a compact sprayer at spraying rate of 1,000 L/ha. Three weeks later, degree of herbicidal effectiveness against weeds and phytotoxicity to the crops were assessed according to the criterion specified above, and the results are presented in Table 2.

TABLE 2

| Compound No. | Dose (g/ha) | Velvet leaf | Amaranthus blitum | Xanthium strumarium | Giant foxtail | Wheat | Maize |
|---|---|---|---|---|---|---|---|
| 9 | 250 | 6 | 8 | 6 | 7 | 0 | 0 |
| 10 | 250 | 7 | 8 | 10 | 8 | 0 | 0 |
| 11 | 250 | 10 | 10 | 10 | 10 | 0 | 0 |
|  | 63 | 9 | 10 | 9 | 10 | 0 | 0 |
| 12 | 250 | 10 | 10 | 10 | 10 | 2 | 5 |
|  | 63 | 10 | 9 | 10 | 10 | 2 | 3 |
| A | 250 | 10 | 10 | 10 | 10 | 10 | 10 |
|  | 63 | 6 | 10 | 10 | 6 | 6 | 6 |

Test Example 2: Foliar Application in Upland Crop (Phytotoxicity Comparison Test on Wheat)

A pot having the opening area of 200 $cm^2$ was filled with soil, and each seeds of plants including wild leaf mustard, Matricaria chamomilla, wild oat, Polygonum convulvulus and wheat are planted onto the surface of the soil. The seeds were then covered with slight amount of soil and were placed in a greenhouse to grow. When each of the plants has grown to a height of from 5 to 25 cm, water dilution of the emulsifiable concentrate specified in the Example 4 and prepared at a desired dose of the active ingredients was sprayed onto the foliar parts of the plants by using a compact sprayer at spraying rate of 1,000 L/ha. Three weeks later, degree of herbicidal effectiveness against weeds and phytotoxicity to the crops were assessed according to the criterion as described above, and the results are presented in Table 3.

TABLE 3

| Compound No. | Dose (g/ha) | Wild leaf mustard | Matricaria chamomilla | Wild Oat | Polygonum convulvulus | Wheat |
| --- | --- | --- | --- | --- | --- | --- |
| 12 | 250 | 10 | 10 | 10 | 10 | 0 |
|  | 63 | 10 | 9 | 10 | 10 | 0 |
| B | 250 | 10 | 10 | 10 | 10 | 4 |
|  | 63 | 10 | 10 | 8 | 10 | 0 |

What is claimed is:

1. Compounds represented by a general formula (1);

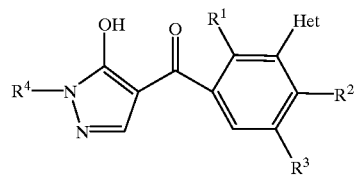

(1)

wherein $R^1$, $R^2$ and $R^3$ each independently represent halogeno, $C_{1-6}$ alkyl, $C_{1-6}$ alkoxy, $C_{1-6}$ haloalkyl, $C_{1-6}$ haloalkoxy, $C_{1-6}$ alkylthio, $C_{1-6}$ alkylsulfinyl or $C_{1-6}$ alkylsulfonyl, $R^4$ and $R^5$ each independently represent hydrogen, $C_{1-6}$ alkyl, $C_{1-6}$ alkenyl or $C_{1-6}$ alkynyl, Het is a substituent represented by the following formula;

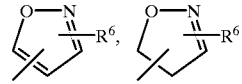

wherein $R^6$ represents hydrogen or $C_{1-4}$ alkyl, and the salts of the compounds.

2. A herbicide comprises one or more of compounds represented by a general formula (1);

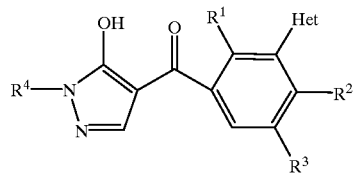

(1)

wherein $R^1$ through $R^5$ and Het are as defined above, and the salts as the active ingredients.

* * * * *

UNITED STATES PATENT AND TRADEMARK OFFICE
CERTIFICATE OF CORRECTION

PATENT NO.    : 6,245,716 B1
DATED         : June 12, 2001
INVENTOR(S)   : Katsunori Tanaka et al.

It is certified that error appears in the above-identified patent and that said Letters Patent is hereby corrected as shown below:

Title page,
Item [75] Inventors, replace "Katsunori Tanaka; Hiroyuki Adachi, both of Odawara; Masami Koguchi, Higashiueno; Akihiro Takahashi, Minamiashigara, all of (JP)
with -- Katsunori Tanaka, Hiroyuki Adachi and Akihiro Takahashi all of Kanagawa; Masami Koguchi of Tokyo, all of (JP) --

Item [57] ABSTRACT and in the claims, column 23,
replace formula (1)

" 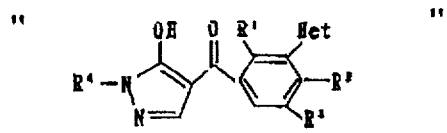 "

with formula (1)

-- 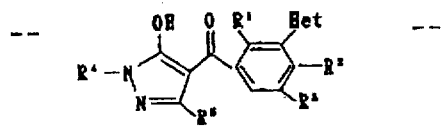 --

Signed and Sealed this

Twelfth Day of February, 2002

*Attest:*

*Attesting Officer*

JAMES E. ROGAN
*Director of the United States Patent and Trademark Office*